United States Patent [19]

VanCleave

[11] 4,335,104
[45] Jun. 15, 1982

[54] ANHYDROUS MULTI-PURPOSE MOISTURIZING COMPOSITION

[75] Inventor: Jon S. VanCleave, West Des Moines, Iowa

[73] Assignee: United Chemical Corporation, Des Moines, Iowa

[21] Appl. No.: 934,097

[22] Filed: Aug. 16, 1978

[51] Int. Cl.$^3$ .................. A61K 7/42; A61K 31/60; A61K 47/00
[52] U.S. Cl. .................. 424/59; 424/DIG. 10; 424/230; 424/358; 424/365
[58] Field of Search .................. 424/59, DIG. 10, 365

[56] References Cited

U.S. PATENT DOCUMENTS

| | | | |
|---|---|---|---|
| 2,241,331 | 5/1941 | Shelton et al. | 424/365 X |
| 2,322,822 | 6/1943 | Brown | 424/365 X |
| 2,372,807 | 4/1945 | Brown | 424/365 |
| 2,404,698 | 7/1946 | Dreyling | 424/365 X |
| 2,675,343 | 8/1954 | Clymer et al. | 424/365 X |

FOREIGN PATENT DOCUMENTS

| | | | |
|---|---|---|---|
| 885716 | 7/1943 | France | 424/184 |
| 1601586 | 10/1970 | France | 424/184 |
| 1199887 | 7/1970 | United Kingdom | 424/195 |

OTHER PUBLICATIONS

The Lancet, 7/1963, vol. II: 7298.
Pail, Aerosol Age, 12/1962, pp. 1 to 4.
Plein et al., Journ. of the Amer. Pharm. Assoc., 2/1953, pp. 79-85.
Plein et al., Journ. of the Amer. Pharm. Assoc., 12/1957, vol. XLVI, No. 12, pp. 705 to 719.
Martindale, The Extra Pharmacopoeia, 1958, vol. I, pp. 695 to 697.
Tajkowski et al., Proceedings of Scientific Section, 12/1953, No. 20, pp. 1-7.

*Primary Examiner*—Dale R. Ore
*Attorney, Agent, or Firm*—Zarley, McKee, Thomte, Voorhees & Sease

[57] ABSTRACT

A multi-purpose anhydrous cosmetic composition which comprises as a major portion, a water insoluble surfactant having a hydrophilic-lipophilic balance of 12 or less, in combination with a small but effective amount of an active ingredient which is soluble in the surfactant. The anhydrous composition is useful as a base material for the making of such cosmetic products as suntan lotions, hand lotions, topical steroids, insect repellants, anti-perspirants, facial lotions, body lotions, therapeutic lotions and the like.

11 Claims, No Drawings

ANHYDROUS MULTI-PURPOSE MOISTURIZING COMPOSITION

BACKGROUND OF THE INVENTION

This invention relates to cosmetic composition products and to the formulation of such products. Some of the products which can be prepared by skilled cosmetic chemical formulators based upon the anhydrous cosmetic lotion of this invention include suntan lotions, facial lotions, hand lotions, body lotions, topical steroid treatment lotions and creams, preshave lotions, rub down lotions, and insect repellants, just to name a few.

Topical products such as those mentioned in the preceding paragraph which are now commercially available, are generally comprised of either oil in water emulsions, water in oil emulsions, all oil soluble products, or all water soluble products. Of course, the oil and water products and likewise, the water and oil products, are emulsions wherein two immiscible components are intimately admixed and emulsified. While there are certain advantages to be obtained from use of either oil in water emulsions, or water in oil emulsions as the base for topical lotions, there are also significant draw backs from the use of such systems. Some of the drawbacks are that the water phase is easily washed off, and if the active ingredient is water soluble, the active ingredient in the topical lotion is washed off; and, therefore the effective treating time of the product is significantly reduced; also, such products often have a slow "rub-in" time. Further, products which contain water as part of the topical lotion base will support the growth of micro-organisms resulting in spoiled or unacceptable products. Therefore, these necessitate the addition of preservatives such as antimicrobial agents. Of course, the addition of such preservatives not only significantly increases the expense of the product, but also the chemical exposure risk to the consumer. Moreover, products which are either oil in water emulsions or water in oil emulsions are in many instances not cosmetically attractive to consumer users because the user recognizes the short life of the product on the skin. Often a negative reaction caused by the lack of desirable skin feel makes the consumer conclude that the product is ineffective, or the product may lack aesthetics.

Additionally, emulsion products based upon oils and water must contain stabilizing emulsifying agents in order to prevent separation into distinct, unsightly layers. Moreover, the microbial attack susceptibility of the water phase makes the propensity for separation even greater in that microbial growth may decrease the emulsion stability.

All oil topical lotions likewise have significant deficiencies in that, in many instances, the consumer does not regard such products as "cosmetically elegant". "Cosmetically elegant", is a term used in the cosmetic formulation art to describe a product which is attractive appearing, has good skin feel, is non-greasy, not tacky, spreadable, and soft. All of these terms generally relate to the consumer user's rating of the product in terms of its attractiveness and skin feel. All oil products are often regarded as not cosmetically elegant in that they tend to have an excessively greasy feel, and often may stain clothing or other items coming into contact with them.

Likewise, water soluble products have certain deficiencies. The primary deficiency of such products is short treating life on the skin since they are easily washed off. Additionally, the products containing large amounts of water, as heretofore explained, are highly susceptible to microbial attack and complications resulting therefrom. Additionally, many water based products are often described by the consumer user as lacking cosmetic elegance. They lack good skin feel, giving an overall impression of wetness, and lack of substantivity, with the consumer paying for a product often containing 60% water, which in itself has no therapeutic value for the skin.

It therefore can be seen that topical lotion products as prepared by cosmetic chemical formulators, generally involve a balancing, and trade off, of the good and bad points of the four basic types of topical lotions: namely oil in water emulsions; water in oil emulsions; oleaginous lotions; or, all water soluble lotions. While each has certain advantages, each also has significant disadvantages. It is for the reason of this balancing and trade off of properties that most formulators for the most part have abandoned all oil and all water soluble products and gone to topical lotion preparations which are either oil in water emulsions or water in oil emulsions.

The fundamental object in preparing such products is to prepare something which is a good emollient, physiologically compatible, a good skin moisturizer, a product which is cosmetically elegant, and a product which has the added benefit of the base topical composition providing for increased and/or prolonged activity of any added active ingredient, such as sun screens, insect repellants, humectants, moisturizers, medicinals or the like.

One fundamentally important criteria by which many such topical lotions must be measured is their ability to act as efficient skin moisturizers.

Skin moisturizing ability is of extreme importance for topical lotions in that consumers regard scaly, dry skin as unsightly and undesirable. Thus, products which are topical lotions and have the added benefit of enhancing skin moisture retention capabilities, have a significant added benefit above and beyond the utility of their active ingredient, whether a sunscreen, an insect repellant, or the like.

Much has been written on the causitive factors for dry and scaly skin. As those skilled in cosmetic formulation theorize, when one speaks of dry and scaly skin, one is speaking of the loss of water from the stratum corneum, which is the outermost dead layer of skin. It is believed that whenever moisture is removed from the stratum corneum, it loses its soft suppleness and becomes dry and scaly. While much has been written about the stratum corneum and its natural moisturizing factor, referred to as "NMF", intensive investigations into the causes of dry skin have largely left only theories to date.

Some cosmetic scientists believe that dryness is due to a loss of the water binding fatty materials from the stratum corneum layer, while others state that dry skin really does not lack water. Most, however, seem to agree that four basic stages are involved in the development of dry skin. In the first stage, there is removal, during cleansing, of the sebum that protects water binding materials in the stratum corneum against being leached out. In the second stage, there is in fact leaching out of the water binding components of the stratum corneum. In the third stage after water evaporation and dehydration, there is a loss of flexibility of the stratum corneum cells. Finally, in the fourth stage, cracking of the stratum corneum occurs, allowing penetration of micro-organisms and irritant materials into the epidermis. In extreme cases, infections, irritations and rashes result.

To date, the state of the art with regard to topical lotions involves reduction of water loss from the stratum corneum by two basic methods. In the first approach to the problem there is a deposit of an occlusive barrier layer to prevent water evaporation from the stratum corneum, the theory being that the deposit of, for example, petrolatum over the stratum corneum will act as a barrier to prevent water escape outwardly therefrom. However, consumer users of such products often do not react favorably to such barrier creation in that they describe it as not cosmetically elegant, greasy, and often sticky. The second approach is to add hygroscopic substances to the stratum corneum in the hope that such substances will draw moisture which will penetrate into the stratum corneum, replacing lost moisture. It is upon this theory that such compounds as sodium lactate and sodium pyrrolidone carboxylic acid (PCA) are often added to topical lotions. Both sodium lactate and sodium pyrolidone carboxylic acid have been reported as naturally occurring in the stratum corneum. The use of such hygroscopic substances, however, has not proven to be effective in providing a beneficial effect.

In summary, an effective topical composition must be an efficient moisturizer and substantive, whatever else it is. An efficient moisturizer may be defined as a substance that overcomes the signs and symptoms of dry skin. This is interpreted by the consumer user as providing a cosmetically elegant skin feel. As can be seen, there are numerous deficiencies with most topical compositions, whether oil in water emulsions, water in oil emulsions, all oil soluble phase or all water soluble phase. If the formulation contains high amounts of water there is a significant danger of bacterial growth and if the product is an emulsion, a danger of emulsion instability. Products containing large amounts of water easily wash off, have a short useful life, a short shelf life, and the water itself from the product contributes nothing to the efficacy.

Moreover, many of the topical lotion products now on the market merely provide a physical barrier which is impervious to moisture, hoping that the skin will retain the moisture it has, rather than providing a physiologically active agent for effective treatment of dry skin that is enduring. Moreover, in many instances in order to provide an enhanced degree of effective moisturization, there must be a corresponding sacrifice of cosmetic elegance.

Accordingly, one object of this invention is to provide an all anhydrous topical composition base.

Another object of this invention is to provide an all anhydrous topical composition base which allows the composition, and any active ingredient which may be added thereto, to maintain cosmetic elegance.

Still another object of this invention is to provide a topical composition which will not support the growth of bacteria.

Yet another object of this invention is to provide a topical composition product which is biodegradable.

An even further object of this invention is to provide a topical composition product which is long lasting on the skin, and results in longer effective treating time for any active ingredient which may be added.

Yet a more specific object of this invention is to provide suntan lotions, hand lotions, topical steroids treating lotions, insect repellants and others which are long lasting, non-polluting, good emollients having increased substantivity, enhanced penetration, and which are effective moisturizing aids for the stratum corneum.

An even further object of this invention is to provide a topical composition product which really does improve from a physiological standpoint, the condition of dry skin and which provides a smooth, velvety, long lasting feel.

The formulations and methods by which the above objects may be accomplished are disclosed in the detailed description of the invention which follows hereinafter.

SUMMARY OF THE INVENTION

This invention relates to a multi-purpose anhydrous cosmetic composition comprising as a major portion of the composition a water insoluble surfactant having a hydrophilic, lipophilic balance of 12 or less, in combination with a small but effective amount of an active ingredient which is soluble in the surfactant. The topical compositions of this invention are believed to be physiologically active for two reasons. The base ingredient which is present as a major proportion is water insoluble and its lipophilic end is attracted to the fatty material of the stratum corneum, thus providing for a product which has a longer skin retention time. However, the molecules of the topical base also have a hydrophilic end which binds moisture. The result is that the base ingredient combines the best of both worlds in terms of both lipophilic characteristics and hydrophilic characteristics. The use of such base compositions provides for physiologically effective treatment of dry skin, provides for increased skin penetration of active ingredients which may be solubilized in the base, and provides for a substantive product. While applicant does not wish to be bound by any theory as to why the compositions work, it is believed that it is because of the hydrophilic, lipophilic balance of the base composition and its binding capacities when absorbed by the skin.

DETAILED DESCRIPTION OF THE INVENTION

As heretofore mentioned, the topical compositions of this invention involve as a major portion a non-ionic surfactant having a hydrophilic-lipophilic balance of 12 or less, preferably 10 or less.

It should be understood by those skilled in the art that also contemplated are mixtures of non-ionic surfactants having an HLB value of 12 or less.

As used herein, the phrase "major portion" contemplates more than the amounts typically used for emulsifying purposes, or as wetting agents, the most common uses for such surfactants. Generally, the term "major portion" can be thought of as involving at least 20% by weight of the entire composition, and more typically at least 35% by weight.

It should also be noted that the systems of the compositions of this invention are anhydrous. Since they lack the presence of water, it is fundamental that the surfactants perform an entirely different function than emulsification and wetting which are only accomplished in water systems.

Typically the amount of the non-ionic surfactant utilized in compositions forming cosmetics or other useful compositions coming within the scope of this invention, is from about 35% by weight of the composition to about 90% by weight of the composition and preferably from about 50% by weight of the composition to about 80% by weight of the composition. Of course, depending upon the ultimate product end use, the precise range of addition will vary within these limits. At levels of less than about 20% by weight of the composition, the significant advantages of the compositions for moisturizing, providing cosmetic elegance, and enhancing the physiological activity of the stratum corneum in order to provide enhanced moisturization will not occur in noticeable amounts. At levels above 90% by weight of the composition, it has been found, primarily by trial and error, that the consumer does not regard the product as cosmetically elegant and characterizes the skin feel as too oily and greasy.

It is important that the non-ionic surfactant have a hydrophilic-lipophilic balance of 12 or less in that as the value increases above 12, it becomes increasingly water soluble and likewise the advantages of the invention are not noted. It is further important that the surfactant be non-ionic, as opposed to either anionic or cationic in that non-ionic surfactants are substantially inert to reactivity with other pharmaceutically active ingredients which might be added to the base composition. Also non-ionics offer significant advantages with respect to compatibility, stability and potential toxicity over other surfactant classes. The most preferred HLB range for the base for the topical lotions of this invention is from about 1.8 to about 8.6.

HLB, as is well known to those skilled in the art, refers to the hydrophile-lipophile balance of a surface active agent, i.e., the balance of the size and strength of the hydrophilic (water-loving or polar) and the lipophilic (oil-loving or non-polar) groups of the agent. Thus, it generally is an arbitrary measure of the relative magnitudes of the polar and non-polar portions of a surface active molecule. Such a relationship greatly influences the molecule and its use. The HLB is in fact an arbitrary scale of values used as a measure of the hydrophilic-lipophilic balance of a given surfactant. The higher the HLB of a surfactant, the more hydrophilic the agent. Typical HLB values can range from as low as a reported value of 1.8 for sorbitan trioleate up to as high as 40 for sodium lauryl sulfate. The choice of the HLB range for the compositions is directly related to the desired attributes for the topical composition.

The preferred surface active, non-ionic agents for this invention can generally be classified as surface active agents which contain an ester or ether linkage at some position within the molecule. Examples include sorbitan fatty acid esters, polyoxyethylene sorbitol esters, polyoxyethylene alcohols, polyoxyethylene cholesterol derivatives, extracts of lanolin alcohols, acetylated lanolin alcohols, lanolin fatty acids, polyunsaturated lanolin esters, and certain other miscellaneous compounds. Furthermore, the following surfactant classes among others have members of which some can be theoretically blended experimentally in various combinations to arrive at the desired HLB of this invention: $C_6$ polyol fatty acid esters such as sorbitan fatty acid esters, polyoxyethylene sorbitol esters, polyoxyethylene alcohols, and poly oxyethylene sorbitan fatty acid esters, and mixed fatty acid ester blends. It is therefore to be understood that this invention contemplates mixtures of surface active agents, with the mixture meeting the previously defined criteria for acceptability.

In particular, those single surface active agents which are known to be useful in the method and composition of this invention include the following: Sorbitan monolaurate which has an HLB of 8.6±1 HLB, and a viscosity at 25° C. of 3,000 cs. and is water insoluble at 25° C. This compound is sold by ICI America, Inc. under the trademark Arlacel 20. Another suitable sorbitan fatty acid ester is sorbitan monolaurate having an HLB of 8.6±1 and a viscosity of 4,250 cs. which also is insoluble in water at 25° C. and sold by ICI America, Inc. under the trademark Span 20.

Suitable polyoxyethylene sorbitol esters for use in the method and composition of this invention include polyoxyethylene sorbitol oleate having an HLB of 9.2±1 HLB and a viscosity at 25° C. of 1800 cs. which is insoluble in water at 25° C. and is sold by ICI America, Inc. under the trademark Atlox 1087. Another compound falling into this category is polyoxyethylene sorbitol tall oil having an HLB of 9.7±1 HLB, a viscosity of 900 cs., an insolubility in water at 25° C. and was sold by ICI America, Inc. under the trademark Atlox 1256. Still another compound suitable for use herein falling into the general category of polyoxyethylene sorbitol esters is a polyoxyethylene sorbitol ester of mixed fatty and resin acids having an HLB of 8.6±1 HLB, and a viscosity at 25° C. of 1900 cs. and is likewise insoluble in water at 25° C. This compound was sold by ICI America, Inc. under the trademark G-1234. Yet another compound falling into the class of polyoxyethylene sorbitol esters suitable for use in this invention is polyoxyethylene sorbitol tallow esters having an HLB of 9.6±1 HLB, a pour point of 18° C. and was sold by ICI America, Inc. under the trademark G-3284.

The only polyoxyethylene alcohol presently known to be usable in the process and composition of this invention is polyoxyethylene (4) lauryl ether having an HLB of 9.7±1 HLB and a viscosity at 25° C. of 35 cs. This compound is water insoluble at 25° C. and is sold by ICI America, Inc. under the trademark Brij 30. Two additional surfactants sold by ICI America, Inc. in the past, but no longer available from them but utilizable herein are polyoxyethylene mannitol dioleate, having an HLB of 8.0±1 HLB and trademarked G-2800 and sorbitan monoleate polyoxyethylene ester mixed fatty and resin acids blend having an HLB of 7.8±1 HLB, a viscosity at 25° C. of 500 cs., and being water insoluble at 25° C. is trademarked G-2684. For further details with regard to each of the compounds mentioned herein, as well as others, see ICI America, Inc. publication 0-1 (LG-60) entitled "General Characteristics of Atlas ® Surfactants" at pages 1 through 9 and publication LD-97 of the same company entitled "The Atlas HLB System" which is specifically incorporated herein by reference.

As can be seen from the above information, HLB is calculated to a statistically significant accuracy of ±1. Thus, for example, an HLB of 9.7±1 falls within the terminology of 10 or less as that term is used herein.

As can be seen from the foregoing description the major portion of the topical compositions for this invention is selected from among the group of non-ionic surfactants meeting the defined hydrophilic-lipophilic balance previously discussed. Amongst the most preferred, but not necessarily limited to those classes of surfactants, are compounds in the classification known as sorbitol, sorbitan and sorbide fatty acid esters, as well as mannitans and mannides. These surfactants are mixtures of partial esters of sorbitol and its anhydrides and are made from fatty acids such as lauric, palmitic, stearic, or oleic acids. These most preferred surfactants, which are the presently known best modes for use in this invention, are sold under the trademarks Span and Arlacel by Atlas Chemical. Since these compounds are surfactants, they have both a hydrophilic moiety in their structure and a lipophilic moiety in their structure.

While not wishing to be bound by any theory of precise mechanism for the action of the non-ionic surfactant in the topical compositions of this invention, it is believed that using these non-ionic surfactants as a major portion in the topical compositions of this invention, promotes the desired attributes and cosmetic elegance of such compositions in accordance with the following: The stratum corneum consists of a hygroscopic lipid component which accounts for its capacity to absorb up to six times its own weight in water; it is believed that the fatty materials of this invention may replenish depleted lipid components. Utilizing a molecule having a hydrophilic complex on the one end and a lipophilic complex on the other end will allow the molecule to penetrate and attach itself to the lipid component of the stratum corneum, and the hydrophilic end will then bind and retain moisture.

The preferred non-ionic surfactants chosen falling within the aforementioned HLB range have a predominantly lipophilic group of end chain moieties. This enables the molecule to firmly attach itself to the fatty substance in the corneum and yields a moiety, stubborn to leave via washing, especially since it is also water insoluble. At the same time, however, the other end of the non-ionic molecule has many hydrophilic end chain moieties capable of absorbing considerable water. Thus, this molecule will attach itself to the lipid component of the corneum and absorb water via its opposing end group moiety. Furthermore, being a surfactant interfacial tension reduction will result. This, in turn, will cause a decrease in the surface free energy and allow water and water vapor to pass more readily from the stratum granulosum to hydrate the stratum corneum and remain there without significant trans-epidermal water loss. Thus, the topical composition base components used in this invention approach the problem of effective moisturization of the stratum corneum from a physiological standpoint, as opposed to merely providing a barrier which hopefully slows down water evaporation, or merely coats the skin surface to provide a smooth feel.

It is not intended that the invention be limited strictly to sorbitan derivatives, but may include other polyoxyethylene non-ionics having the preferred HLB criteria mentioned herein. As previously mentioned, a multitude of topical products may be made using as a "major portion" the non-ionic surfactants meeting the criteria previously set forth herein. The exact composition will depend, as those of ordinary skill in the art of cosmetic formulation know, upon the ultimate purpose of use for the topical preparation. Some examples of suitable compositions which can be prepared utilizing the invention are suntan lotions, facial lotions, body lotions, topically applied steroid containing lotions, hand lotions, medicated lotions, rub down lotions, pre-shave lotions, antiperspirants and other topicals such as insect repellants, specialty preparations such as hormone preparations, acid/astringent preparations, lubricating creams, night creams, cream rouge, and bath oil blends. Those which have shown significant improvement include the preferred compositions for suntan lotions, insect repellants, topical steroids and hand lotions.

The basic ingredients of such compositions are well known to cosmetic formulators of ordinary skill in the art. The topical base may be used effectively in virtually all such compositions. With regard to suntan lotions, such lotions typically are comprised of a diluent such as propylene glycol, an emollient such as isopropyl myristate and a preservative, and in addition a sunscreen. Typical examples of sunscreens include paraamino benzoic acid and derivatives thereof such as octydimethyl para amino benzoic acid, homosalate, amyldimethyl para-amino benzoic acid, oxybenzone glycerol, para-amino benzoic acid and sulisobenzone. Such suntan composition also often employ skin aids such as aloe, cocoa butter, proteins and perhaps lubricating ingredients such as silicone compounds, and of course, as minors, fragrances and perfumes.

For further details with regard to precise sun product formulations, see *Cosmetic and Toiletries,* March 1976 pages 81 through 94 which are specifically incorporated herein by reference.

Certain formulations for suntan topical compositions which have been found effective in this invention are as follows:

| Ingredient | Range of Added Amount | Preferred Range |
|---|---|---|
| Non-ionic surfactant base having an HLB of 12 or less | 40-90% | 50%-70% |
| Diluent, such as propylene glycol | 5-60% | 20%-40% |
| Sunscreen, such as octyl-dimethyl paraminobenzoic acid | 1-10% | 2%-5% |
| Emollient and/or skin aid, such as aloe | 1-30% | 3%-10% |
| Lubricating additive such as silicone fluids, like Dow 556 | Up to 25% | 1%-5% |
| Minors, such as fragrances and perfumes | Up to 3% | .25-2% |

With regard to hand lotions, typical hand lotions employing the topical lotion base of this invention may be made within the following formulation ranges:

| Ingredient | Range of Addition on Percent Weight Basis | Preferred Range |
|---|---|---|
| Non-ionic surfactant having an HLB of 12 or less | 40-90% | 50-70% |
| Diluent, such as propylene glycol | 5-70% | 20-40% |
| Skin treatment aids such as aloe | Up to 80% | 5-20% |
| Lubricant additive such as silicone fluids like Dow 556 | Up to 10% | 1-5% |
| Minors, such as preservatives and fragrance | Up to 5% | .25-2% |

The purpose of the addition of a diluent such as propylene glycol is that it allows the non-ionic to be more cosmetically elegant and enhances its penetration, as well as contributing its own humectant qualities to the preparation. Dow Chemical Silicone 556 provides a lubricant quality as well as an anti-stickiness factor.

A typical composition for a rub down lotion employing for non-ionic surfactant of this invention is as follows:

| Ingredient | Range of Addition | Preferred |
|---|---|---|
| Non-ionic surfactant having an HLB of 10 or less | 40-90% | 50-80% |

-continued

| Ingredient | Range of Addition | Preferred |
| --- | --- | --- |
| Counter-irritant and diluent which provides warming sensation such as methyl salicylate | 5-40% | 10-35% |
| Diluent, such as propylene glycol | Up to 60% | 5-40% |
| Silicone | Up to 10% | 1-5% |

With regard to insect repellants, as those skilled in the art know, a variety of active ingredients may be utilized as repellants. The only criteria for employment with this invention is that the repellant be soluble in the non-ionic surfactant. Suitable compositions can be made as follows:

| Ingredient | Range of Addition |
| --- | --- |
| Metadelphene (N,N-dimethyl-m-toluamide) | .5-50% |
| N-octyl bicychoheptane di carlioximide | .5-10% |
| 2,3:4,5-Bis (2-butylene) tetra hydro-2-furaldrhyals | 0.1-5% |
| Di-n-propyl isocinchomcronate | 0.1-5% |
| Isopropyl alcohol | 25-45% |
| Non-ionic surfactant having HLB of 12 or less | 20-50% |
| Silicone fluid such as Dow 556 | 1-5% |
| Fragrances | .25-2% |

As heretofore mentioned, the base topical lotions of this invention may also be used as effective carriers for topical steroids. Thus, corticosteroids such as the one sold under the trademark Topicort ® of Hoechst-Roussel Pharmaceuticals, Inc. of Somerville, N.J. may be employed with the lotions of this invention. Topicort, contains a corticosteroid known as desoximetasone and is used commonly at levels such as 0.25% in emollient creams and the like. Suitable formulations for topical steroid treatments are as follows:

| Ingredient | Range |
| --- | --- |
| Non-ionic surfactant having an HLB of 12 or less | 40-90% |
| Diluent such as propylene glycol | 5-70% |
| Lubricating additive, such as silicone fluids like Dow 556 | 1-5% |
| Minors such as preservatives and fragrance | Up to 5% |
| Corticosteriod | Up to 1% |

The following examples of the preparation and use of hand/facial lotions, suntan lotions, a rub down lotion and an insect repellant are offered as illustrative examples of employing the topical lotion basis of this invention.

EXAMPLE 1

(Hand/Facial Lotion)

| Ingredient | Percent Weight Basis |
| --- | --- |
| Arlacel 20 (sorbitan mono-laurate HLB 8.6 ± 1, viscosity at 25° C., 3000 cs. | 59% |
| Propylene glycol | 33% |
| Aloe | 6% |
| Dow Corning 556 Cosmetic grade polyphenyl-methyl siloxane fluid | 1% |
| fragrance | 1% |

Propylene glycol allows the non-ionic surfactant of this invention to be more cosmetically acceptable and enhances penetration as well as contributes its own humectant qualities to the preparation. The Dow silicone fluid provides a lubricity quality as well as anti-stickiness factor to the preparation. When applying this lotion to the hands, it has been found that this formula is characterized by consumer users as very softening and moisturizing to the skin upon initial application. With washing and subsequent toweling the skin feels yet more velvety as though it has absorbed water like a sponge. The formula resists washing even with mild soap for approximately 24 hours.

As can be understood by those of ordinary skill in the art, this hand lotion may have incorporated therein other skin medicinals (including vitamins), emollients, other humectants, certain solvents, penetrants and other skin aids.

Unanimously all users of the product commented that it imparted excellent skin feel.

The product was prepared by simply intimately admixing all of the above ingredients.

EXAMPLE 2

Suntan Lotion

| Ingredient | Percent Weight Basis |
| --- | --- |
| Arlacel 20 | 60.50% |
| Propylene glycol | 30.0% |
| Octyldimethyl paramino benzoic acid | 3.50% |
| Aloe | 4.00% |
| Dow Corning 556 | 1.00% |
| fragrance | 1.00% |

When the above suntan formulation, which was prepared by simply admixing all of the ingredients to an intimate admixture, was utilized by swimmers and sunbathers, the users remarked about the excellent "skin feel" of the tanning lotion when they were in the water. Moreover, the product did not wash off during swimming as is common with most suntan lotions. The swimmers or bathers found the product to be equally as effective for sunscreen effectiveness as other suntan lotions they have previously used.

EXAMPLE 3

Rub Down Lotion

| Ingredient | Percent Weight Basis |
| --- | --- |
| Span 20 | 64.30% |
| Methyl salicylate | 31.00% |
| Propylene glycol | 4.70% |

Users of this product remarked of its excellent skin feel, the fact that it stayed with them even after showering, and that it was effectively relaxing.

EXAMPLE 4

Insect Repellant

| Ingredient | Percent Weight Basis |
| --- | --- |
| Metadelphine (N,N-diethyl-M- | 17.50% |
| MGK 264 (N-octyl-bicycloheptene bicarboximide) | 5.00% |
| MGK 11 (2, 3:4, 5-Bis (2-butylene) tetrahydro-2-furaldehyde | 1.25% |
| MGK 326 - Di-n-propyl isocinchomeronate | 1.25% |

-continued

| Ingredient | Percent Weight Basis |
|---|---|
| IPA 99 (Isopropyl alcohol) | 36.25% |
| Span 20 | 37.50% |
| Dow Corning 556 | 1.00% |
| Fluid and fragrance | 2.50% |

The insect repellant was used and found to be effective and maintained its effectiveness even after moderate washing. In comparative tests with other repellants effectiveness was increased on an hours basis of from 30% to 100%.

As those skilled in the art of cosmetic formulation know, there is no precise criticality with the method of addition of the ingredients to form compositions coming within the scope of this invention. The ingredients are all simply added together in any manner chosen, and intimately admixed by suitable known mixing means.

All of the products made in Examples 1 through 4 were found by the users to be long lasting, to provide effective skin moisturization, to be good emollients, to be cosmetically elegant, and to provide excellent skin feel. Moreover, since the products were all non-aqueous, they had no susceptibility to microbial attack, did not separate upon standing, exhibited long lasting treating life during use, and exhibited good shelf life during observation over some period of time. Moreover, the products in comparison with other emulsion products utilized by consumers were preferred almost on a unanimous basis by the users. It can therefore be seen that the invention has accomplished at least all of its stated objectives.

What is claimed is:

1. A multi-purpose anhydrous topical cosmetic composition comprising from about 20% to about 90% of a water insoluble non-ionic surfactant or blend of surfactants, the molecules of which have a hydrophilic portion and a lipophilic portion and have a hydrophilic-lipophilic balance of 12 or less, in combination with a small but effective amount of an active ingredient which is soluble in said surfactant.

2. The anhydrous cosmetic composition of claim 1 wherein said water insoluble surfactant has an HLB value of 10 or less.

3. The anhydrous cosmetic composition of claim 1 wherein said water insoluble surfactant has an HLB value of from about 1.8 to about 8.6.

4. The composition of claim 1 wherein the amount of said water insoluble surfactant is from about 35% to about 90% by weight of said anhydrous cosmetic composition.

5. The anhydrous cosmetic composition of claim 4 wherein the amount of said water insoluble surfactant portion of said composition is from about 50% to about 80% by weight of said composition.

6. The composition of claim 1 wherein said water insoluble surfactant is a surfactant, or mixtures of surfactants, derived from $C_6$ polyol fatty acid esters.

7. The compositions of claim 6 wherein said $C_6$ polyol fatty acid esters are selected from the group consisting of sorbitol fatty acid esters, sorbitan fatty acid esters, sorbide fatty acid esters, mannitol fatty acid esters, mannitan fatty acid esters, and mannide fatty acid esters.

8. The compositions of claim 7 wherein the fatty acids from which said fatty acid esters are derived are selected from lauric acid, patmitic acid, stearic acid and oleic acid.

9. An anhydrous topical suntan composition consisting of from about 40% to about 90% by weight of a non-ionic surfactant base or blends thereof, the molecules of which have a hydrophilic portion and a lipophilic portion and a hydrophilic-lipophilic balance of 12 or less, from about 5% to about 60% by weight of a non-aqueous diluent, from about 1% to about 10% by weight of a sunscreen, from about 1% to about 30% by weight of an emollient, from about 1% to about 5% by weight of a lubricating additive, and from about 0.25% to about 2% by weight minors.

10. An anhydrous hand lotion topical cosmetic composition comprising
from about 40% to about 90% by weight of a non-ionic surfactant or blends thereof the molecules of which have a hydrophilic portion and a lipophilic portion and a hydrophilic-lipophilic balance of 12 or less.,
from about 5% to about 70% by weight of a non-aqueous diluent,
from about 5% to about 20% by weight of a skin treatment aid,
from about 1% to about 5% of a lubricant additive, and
from about 0.25% to about 2% minors.

11. An anhydrous topical insect repellant composition comprising
from about 20% to about 50% of a non-ionic surfactant base or blends thereof, the molecules of which have a hydrophilic portion and a lipophilic portion and
a hydrophilic-lipophilic balance of 12 or less,
from about 1% to about 5% of a lubricating additive,
from about 0.25% to about 2% fragrances, with the balance comprising active insect repellant which is soluble in said non-ionic surfactant, and a suitable non-aqueous carrier therefor.

* * * * *